United States Patent
Welle et al.

(10) Patent No.: US 9,688,792 B2
(45) Date of Patent: Jun. 27, 2017

(54) USE OF A METALLOCENE CATALYST TO PRODUCE A POLYALPHA-OLEFIN

(71) Applicant: TOTAL RESEARCH & TECHNOLOGY FELUY, Seneffe (Feluy) (BE)

(72) Inventors: Alexandre Welle, Court-St-Etienne (BE); Jeroen Wassenaar, Huizingen (BE); Martine Slawinski, Nivelles (BE)

(73) Assignee: Total Research & Technology Feluy, Feluy (Seneffe) (BE)

( * ) Notice: Subject to any disclaimer, the term of this patent is extended or adjusted under 35 U.S.C. 154(b) by 0 days.

(21) Appl. No.: 14/725,540

(22) Filed: May 29, 2015

(65) Prior Publication Data

US 2015/0344598 A1   Dec. 3, 2015

(30) Foreign Application Priority Data

May 30, 2014 (EP) .................................... 14170548

(51) Int. Cl.
*C08F 4/6592* (2006.01)
*C08F 10/14* (2006.01)
*C07F 17/00* (2006.01)
*C08F 110/14* (2006.01)
*C08F 4/659* (2006.01)
*C07C 2/34* (2006.01)
*C07C 5/03* (2006.01)
*B01J 31/22* (2006.01)

(52) U.S. Cl.
CPC .............. *C08F 110/14* (2013.01); *C07C 2/34* (2013.01); *C07C 5/03* (2013.01); *C07F 17/00* (2013.01); *C08F 4/65908* (2013.01); *C08F 4/65912* (2013.01); *C08F 4/65927* (2013.01); *B01J 31/2295* (2013.01); *B01J 2531/48* (2013.01); *C07C 2521/04* (2013.01); *C07C 2521/08* (2013.01); *C07C 2523/42* (2013.01); *C07C 2523/44* (2013.01); *C07C 2523/755* (2013.01); *C07C 2523/882* (2013.01); *C07C 2531/14* (2013.01); *C07C 2531/22* (2013.01); *C08F 10/14* (2013.01)

(58) Field of Classification Search
CPC .............. C08F 4/65927; C08F 4/65908; C08F 4/65912; C08F 10/00; C08F 10/14; C07F 17/00
See application file for complete search history.

(56) References Cited

U.S. PATENT DOCUMENTS

| | | | |
|---|---|---|---|
| 2003/0055184 A1 | 3/2003 | Song et al. | |
| 2003/0232937 A1 | 12/2003 | DiMaio | |
| 2009/0221775 A1* | 9/2009 | Hagemeister | C08F 10/00 526/183 |
| 2010/0292424 A1* | 11/2010 | Wu | C10M 107/10 526/170 |
| 2012/0053309 A1 | 3/2012 | Holtcamp et al. | |

FOREIGN PATENT DOCUMENTS

| | | |
|---|---|---|
| EP | 0279586 A2 | 8/1988 |
| EP | 1164146 A2 | 12/2001 |
| WO | 0214384 A2 | 2/2002 |
| WO | 2007/011462 A1 | 1/2007 |
| WO | 2007011459 A1 | 1/2007 |
| WO | 2009/097069 A1 | 8/2009 |
| WO | 2012134688 A1 | 10/2012 |

OTHER PUBLICATIONS

Extended European Search Report issued in Application No. 14170548.3, dated Aug. 14, 2014, 4 pages.
Il Kim, et al, "Higher α-Olefin Polymerizations Catalyzed by rac-Me2Si(1-C5H2-2-CH3-4-tBu)2Zr(NMe2)2/Al(iBu)3/[Ph3C][B(C6F5)4]"; Journal of polymer science: Part A: Polymer Chemistry 2000, vol. 38, pp. 1687-1697.
Search Report issued in Great Britain Application No. 1509242.2, dated Feb. 26, 2016, 2 pages.
Office Action issued in French Application No. 1501116, dated Feb. 26, 2016, 6 pages.
Communication issued in European Application No. 15725026.7, dated Apr. 18, 2017, 4 pages.

* cited by examiner

*Primary Examiner* — Caixia Lu
(74) *Attorney, Agent, or Firm* — Albert Shung

(57) ABSTRACT

A process may include contacting an olefin monomer and a racemic bridged metallocene catalyst at a temperature of 80° C. to 150° C. in the presence of hydrogen. The racemic bridged metallocene catalyst may include a metallocene compound (A) and an activator component (B). The process may include recovering an effluent containing polyalpha-olefins (PAOs). The metallocene compound (A) may be represented by the formula $R(Cp_1)(Cp_2)MX_1X_2$. In the formula, R may be a $C_1$-$C_{20}$ alkylene bridging group; $Cp_1$ and $Cp_2$ may be the same or different substituted or unsubstituted tetrahydroindenyl rings; M may be a transition metal; and $X_1$ and $X_2$ may be independently selected from hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, substituted germylcarbyl radicals.

27 Claims, No Drawings

USE OF A METALLOCENE CATALYST TO PRODUCE A POLYALPHA-OLEFIN

CROSS-REFERENCE TO RELATED APPLICATIONS

This application is claims priority from European Patent Application No. 14170548.3, filed on May 30, 2014, the entirety of which is incorporated herein by reference.

FIELD OF THE INVENTION

The invention relates to the use of a racemic bridged metallocene catalyst to produce polyalpha-olefins (PAOs).

BACKGROUND OF THE INVENTION

Polyalpha-olefins (PAOs) comprise a class of hydrocarbons manufactured by the catalytic oligomerization of olefins such as $C_2$-$C_{20}$ alphaolefins. PAOs have achieved an importance in the lubricating oil market as they can be used as basestocks useful for synthetic lubricants. With this application in mind, the research efforts have generally focussed on fluids exhibiting useful viscosities over a wide range of temperature, such as improved viscosity index (VI). The viscosity index is an empirical number which indicates the rate of change in viscosity of an oil within a given temperature range. High viscosity index is usually desirable because the oil will have higher viscosity at higher temperature, which translates into better lubrication and better protection of the contacting machine elements. The viscosity index (VI) is calculated according to ISO2009.

Processes for producing PAOs are known from the art. The oligomerization of PAOs in presence of metallocene catalysts has been described for example in WO02/14384. This document discloses the use of CpFlu catalysts for the oligomerisation of PAO. CpFlu catalysts are metallocene catalysts incorporating a cyclopentadienyl-fluorenyl structure. Comparative examples J and K are directed to the use of racemic bridged metallocene catalysts such as rac-ethyl-bis(indenyl)zirconium dichloride or rac-dimethylsilyl-bis(2-methyl-indenyl)zircomium dichloride in combination with methylalumoxane (MAO) at 40° C. (at 200 psi hydrogen or 1 mole of hydrogen) to produce isotactic polydecene reportedly having a $KV_{100}$ of 702 cSt, and a viscosity index of 296; or to produce polydecene reportedly having a $KV_{100}$ of 1624, and a viscosity index of 341, respectively.

In several applications it is preferred to obtain PAOs with a low kinematic viscosity at 100° C. ($KV_{100}$). Thus it is looked for PAOs with a low $KV_{100}$ combined with a good viscosity index. Such compromise may be achieved in promoting the production of 11-octyldocosane within the trimer fraction. Indeed, the presence of this component is beneficial for fluid property, as it allows better viscometrics ($KV_{100}$ and viscosity index). WO2007/011459 discloses the oligomerisation of alpha-olefin into a PAOs containing 11-octyldocosane within the trimer fraction. Among others, the use of rac-dimethysilylbis(tetrahydroindenyl)zirconium dichloride in an oligomerisation process without the addition of hydrogen during the oligomerization step is disclosed. Also it discloses obtaining oligomers with high degree of unsaturated bonds. However, it does not disclose obtaining oligomers with kinematic viscosity $KV_{100}$ of at most 10 cSt as measured according to ASTM D445 at 100° C. together with a viscosity index of more than 160.

Another problem encountered in the prior art is to conduct oligomerization reactions with a good catalyst activity. Indeed, it has been observed that the production of low kinematic viscosity products is accompanied by a loss in the catalyst activity.

Thus there is still a need to produce PAOs having good viscometrics (i.e. a good compromise between kinematic viscosity and viscosity index) together with a good catalyst activity.

SUMMARY

The use according to the invention is directed to a single site metallocene catalyst to produce with a good catalyst activity a polyalpha-olefin (PAO) at high temperature in the presence of hydrogen, the PAO having a low kinematic viscosity and a high viscosity index. This PAO comprises dimer, trimer, tetramer and optionally higher oligomer products. A single site metallocene catalyst is defined as a catalyst which contains a single metal center.

The use according to the invention is related to a racemic bridged metallocene catalyst composed of a metallocene compound (A) and an activator component (B) in a process to produce a polyalpha-olefins (PAOs) comprising the steps of:

contacting in the presence of hydrogen, a monomer and the metallocene catalyst composed of a metallocene compound (A) and an activator component (B), at a temperature of 80° C. to 150° C.;

recovering an effluent containing polyalpha-olefins (PAOs)

wherein the metallocene compound (A) is represented by the formula

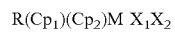

$$R(Cp_1)(Cp_2)M\ X_1X_2$$

wherein

R is a $C_1$-$C_{20}$ alkylene bridging group;

$Cp_1$ and $Cp_2$ are the same or different substituted or unsubstituted tetrahydroindenyl rings, wherein if substituted, the substitutions may be independent and/or linked to form multicyclic structures;

M is a transition metal selected from the group consisting of titanium, zirconium and hafnium;

$X_1$ and $X_2$ are independently hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, substituted germylcarbyl radicals; or both $X_1$ and $X_2$ are joined and bound to the metal atom to form a metallacycle ring containing from 3 to 20 carbon atoms.

DETAILED DESCRIPTION OF INVENTION

Before the present use according to the invention is described, it is to be understood that this invention is not limited to particular methods, components, or devices described, as such methods to be achieved, components, and devices may, of course, vary. It is also to be understood that the terminology used herein is not intended to be limiting, since the scope of the present invention will be limited only by the appended claims.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in another embodiment" in various places throughout this specification are not necessarily all referring to the same embodiment, but may do so. Furthermore, the particular features, structures or characteristics may be combined in any manner as long as they are not obviously incompatible, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Catalyst

Useful metallocene catalysts according to the invention are composed of a metallocene compound (A) and an activator component (B).

Useful metallocene compounds (A) are bridged and substituted or un-substituted. Useful metallocene compounds (A) are racemic and represented by the formula

$$R(Cp_1)(Cp_2)M\ X_1X_2 \qquad (1)$$

wherein

R is a $C_1$-$C_{20}$ alkylene bridging group;

$Cp_1$ and $Cp_2$ are the same or different substituted or unsubstituted tetrahydroindenyl rings, wherein if substituted, the substitutions may be independent and/or linked to form multicyclic structures;

M is a transition metal selected from the group consisting of titanium, zirconium and hafnium;

$X_1$ and $X_2$ are independently hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, substituted germylcarbyl radicals; or both $X_1$ and $X_2$ are joined and bound to the metal atom to form a metallacycle ring containing from 3 to 20 carbon atoms.

In an embodiment, in the metallocene compound (A), R is a $C_1$-$C_{20}$ alkylene bridging group, R is preferably selected from the group consisting of methylene (—CH$_2$—), ethylene (—CH$_2$—CH$_2$—), methylmethylene (—CH(CH$_3$)—), 1-methyl-ethylene (—CH(CH$_3$)—CH$_2$—), n-propylene (—CH$_2$—CH$_2$—CH$_2$—), 2-methylpropylene (—CH$_2$—CH (CH$_3$)—CH$_2$—), 3-methylpropylene (—CH$_2$—CH$_2$—CH (CH$_3$)—), n-butylene (—CH$_2$—CH$_2$—CH$_2$—CH$_2$—), 2-methylbutylene (—CH$_2$—CH(CH$_3$)—CH$_2$—CH$_2$—), 4-methylbutylene (—CH$_2$—CH$_2$—CH$_2$—CH(CH$_3$)—), pentylene and its chain isomers, hexylene and its chain isomers, heptylene and its chain isomers, octylene and its chain isomers, nonylene and its chain isomers, decylene and its chain isomers, undecylene and its chain isomers, dodecylene and its chain isomers. More preferably, R is ethylene.

In another embodiment, in the metallocene compound (A), M is zirconium.

In a preferred embodiment the metallocene compound (A) is selected from racemic ethylene bis(tetrahydroindenyl) zirconium dimethyl and racemic ethylene bis(tetrahydroindenyl)zirconium dichloride. Preferably the metallocene compound (A) is racemic ethylene bis(tetrahydroindenyl) zirconium dimethyl.

Useful activator component (B) may be selected from alumoxane or ionic activators. Preferably the activator component is an ionic activator.

In an embodiment, the activator component (B) is an alumoxane selected from methylalumoxane, modified methyl alumoxane, ethylalumoxane, isobutylalumoxane, or any combination thereof. Preferably the activator component (B) is methylalumoxane (MAO).

The alumoxane activator is generally an oligomeric compound containing —Al(R1)-O— sub-units, where R1 is a $C_1$-$C_{20}$ alkyl group being cyclic or linear. Alumoxane activators are well known to the man skilled in the art, and their method of preparation is for example described in EP 0 279 586. When an alumoxane or modified alumoxane is used the activator/catalyst molar ratio (i.e. Al/Zr ratio) is preferably ranging from 10 to 3,000, more preferably from 50 to 2,000, most preferably from 100 to 1,500.

In another embodiment, the activator component (B) is an ionic activator selected from dimethylanilinium tetrakis(perfluorophenyl)borate, triphenylcarbonium tetrakis(perfluorophenyl) borate, dimethylanilinium tetrakis(perfluorophenyl) aluminate, or any combination thereof. Preferably the ionic activator is dimethylanilinium tetrakis(perfluorophenyl)borate. When an ionic activator is used the activator/catalyst molar ratio is preferably ranging from 0.5 to 4; preferably from 0.8 to 1.2.

The ionic activator may be used in combination with a co-activator which is a trialkylaluminium, or an alumoxane such as methylalumoxane. Preferably the co-activator is a trialkylaluminium selected from Tri-Ethyl Aluminum (TEAL), Tri-Iso-Butyl Aluminum (TIBAL), Tri-Methyl Aluminum (TMA), and Methyl-Methyl-Ethyl Aluminum (MMEAL), more preferably the co-activator is Tri-Iso-Butyl Aluminum (TIBAL). When a co-cativator is used the co-activator/catalyst molar ratio is preferably ranging from 10 to 1000, preferably from 50 to 500, more preferably from 100 to 400.

The activation of the metallocene catalyst is achieved by combining the metallocene compound (A) with the activator component (b) either simultaneously or in any sequence and with any interval of time there between and either within the presence of, or in absence of, the olefin monomer(s) and hydrogen. Preferably the activated metallocene catalyst is prepared in advance and thereafter introduced into the oligomerization reactor with the olefin monomer(s) in the presence of hydrogen.

Olefin Monomers

The use of the metallocene catalyst according to the invention is in the oligomerization of $C_2$ to $C_{20}$ olefins, preferably $C_6$ to $C_{14}$. Preferred olefins monomers may be one or more selected from 1-hexene, 1-heptene, 1-octene, 1-nonene, 1-decene, 1-dodecene, 1-undecene and 1-tetradecene. With preference, the monomer is 1-decene. The oligomerization according to the invention is a homo-oligomerization or a co-oligomerization, preferably the oligomerization is a homo-oligomerization. In one embodiment, the olefin is 1-decene and the polyalpha-olefins (PAOs) obtained is a mixture of dimers, trimers, tetramers and pentamers (and higher) of 1-decene.

Oligomerization Process

The oligomerization processes, such as solution, slurry and bulk oligomerization, and the reactor types used for metallocene-catalyzed oligomerizations may be used in the invention. In a preferred embodiment, the olefin monomer(s) are contacted with the metallocene compound and the activator component in the solution phase or bulk phase, preferably in a batch mode.

According to the invention the temperature of the reactor used is from 50° C. to 200° C., preferably from 70° C. to 160° C., more preferably from 80° C. to 150° C., even more preferably from 100° C. to 130° C.

In a preferred embodiment, the hydrogen partial pressure in the reactor is from 0.1 to 20 bar, preferably from 1 to 6 bar.

In another embodiment, the reaction time of the metallocene catalyst in the reactor is from 2 min to 5 hours, preferably from 5 min to 3 hours, more preferably from 30 min to 2.5 hours.

In another embodiment, solvents or diluents are present in the reactor. If present, solvents or diluents are selected from straight and branched chain hydrocarbons such as butanes, pentanes, hexanes, heptanes, octanes, and the like, cyclic and alicyclic hydrocarbons such as cyclopentane, cyclohexane, cycloheptane, methyl-cyclopentane, methylcyclohexane, methylcycloheptane and the like, and alkyl-substituted aromatic compounds such as toluene, xylene, and the like and mixtures thereof.

In a preferred embodiment, a step of conducting a hydrogenation reaction is performed before recovering an effluent containing polyalpha-olefin (PAO). Said step is performed using a hydrogenation catalyst.

In another embodiment, the hydrogenation catalyst is selected from nickel supported on kieselguhr, or platinum or palladium supported on alumina, or cobalt-molybdenum supported on alumina, preferably the hydrogenation catalyst is palladium supported on alumina.

In another embodiment, the reaction time of the hydrogenation catalyst in the reactor is from 2 min to 10 hours, preferably from 30 min to 5 hours.

In another embodiment, the hydrogenation reaction is performed with a ratio $H_2$/monomer of at least 100 ppm, and preferably below 600 ppm.

In another embodiment, the hydrogenation reaction is conducted at a temperature ranging from 50° C. to 200° C., preferably from 60° C. to 150° C., more preferably from 70° C. to 140° C., even more preferably from 80° C. to 120° C.

In another embodiment, the hydrogenation reaction is conducted at a hydrogen pressure ranging from 5 to 50 bar, preferably from 10 to 40 bar, more preferably from 15 to 25 bar.

The oligomerization reaction can be run in batch mode, where all the components are added into a reactor and allowed to react to a degree of conversion, either partial or full conversion. Subsequently the catalyst is deactivated by any possible means, such as exposure to air or water, or by addition of alcohols or solvents containing deactivating agents. The oligomerization can also be carried out in a semi-continuous operation, where feeds and catalyst system components are continuously and simultaneously added to the reactor so as to maintain a constant ratio of catalyst system component to feed olefin(s). When all feeds and catalyst components are added, the reaction is allowed to proceed to a predetermined stage. The reaction is then discontinued by catalyst deactivation in the same manner as described for batch operation. The oligomerization can also be carried out in continuous operation, where feeds and catalyst system components are continuously and simultaneously added to the reactor so as to maintain a constant ratio of catalyst system and feeds. The reaction product is continuously withdrawn from the reactor, as in a typical continuous stirred tank reactor (CSTR) operation.

A typical batch solution oligomerization process can be carried out by first introducing the olefin monomer, preferably 1-decene, either alone or in combination with an optional hydrocarbon solvent, for example hexane, into a stirred tank reactor. If a co-oligomerization is desired, the additional liquid olefin monomer, for example 1-octene, is added simultaneously or sequentially with the other monomer. The reactor is brought up to the desired temperature, for example from 80° C. to 150° C., and a measured amount of hydrogen is then introduced into the stirred tank reactor. If copolymerization is desired with a gaseous monomer, a monomer feed is then sparged into the liquid phase, either in combination with, or separate from hydrogen feed. By carrying out the oligomerization reaction in the presence of hydrogen the kinematic viscosity of the polyalpha-olefin produced is lowered compared to the kinematic viscosity obtained in the same oligomerization reaction in the absence of hydrogen.

Once the desired conditions are established, the metallocene catalyst, in the required amounts, is added to the liquid phase in the reactor. The rate of oligomerization is controlled by the concentration of the catalyst and olefin monomer(s) present or added during oligomerization. In an embodiment, nothing is added into the reactor during the oligomerization reaction. In another embodiment, the initial reactor pressure in the reactor is maintained by a constant flow of hydrogen, inert gas, gaseous monomer(s) or a combination thereof. The reaction time in the reactor is for example from 1 hour to 3 hours. The catalyst is then deactivated by conventional means, such as for example the introduction of isopropanol into the reactor.

The hydrogenation catalyst, preferably palladium supported on alumina, is then introduced into the reactor. The reaction time in the reactor is for example from 2 hours to 4 hours. The reactor is then depressurized and an effluent containing the polyalpha-olefins is recovered. The hydrogen pressure, the hydrogenation catalyst concentration and/or the reaction time are parameters the value of which can be increased in order for the hydrogenation reaction to be completed. Hydrogenated PAOs can be used as obtained or further distilled or fractionated to the right component if necessary. For example the C30 fraction can be isolated by distillation using ASTMD2892 under 0.5 mmHg partial pressure as a cut having an atmospheric equivalent boiling temperature range from 350 to 440° C.

The polyalpha-olefins obtained by the oligomerization process have improved combination of molecular weight (Mw), molecular weight distribution (Mw/Mn), kinematic viscosity ($KV_{100}$), and viscosity index (VI).

Oligomers

For the purpose of the disclosure, the term oligomer refers to compositions having from 2 to 75 mer units and the term polymer refers to compositions having 76 or more mer units. A mer is defined as a unit of an oligomer that originally corresponded to the olefin(s) used in the oligomerization or polymerization reaction. For example, the mer of polydecene would be decene.

The product properties, including molecular weight and Mw/Mn, were analyzed by gel permeation chromatography (GPC) using tetrahydrofuran (THF) as the solvent and polystyrene as the calibration standard. 1,3,5-trichlorobenzene (TCB) was used as solvent for determining molecular weights of high viscosity PAOs.

In another embodiment, the polyalpha-olefins obtained by the use according to the invention preferably have a Mw of 30,000 Da or less; preferably from 200 to 30,000 Da; preferably from 500 to 10,000 Da; preferably from 800 to 7,000 Da and more preferably from 1,000 to 4,000 Da.

In another embodiment, the polyalpha-olefins obtained by the use according to the invention preferably have a Mw/Mn of greater than 1 and less than 5, preferably less than 4, preferably less than 3, more preferably less than 2.5.

The Mw is correlated to the kinematic viscosity at 100° C. in cSt for fluids prepared in this invention using 1-decene as feed by the following relationships:

if Mw>2000 Da: Calc KV 100 (cSt)=(0.0239×Mw)−49.581; and

If 1500 Da<Mw<2000 Da: Calc KV 100 (cSt)=(0.0079×Mw)−5.5342

Unless otherwise indicated the kinematic viscosity is measured according to ASTM D445 at 100° C. and not calculated from the Mw.

In another embodiment, the polyalpha-olefins obtained by the use according to the invention preferably have a kinematic viscosity at 100° C. from 2 to 50 cSt, preferably from 3 to 30 cSt, more preferably from 3 to 10 cSt as measured according to ASTM D445 at 100° C.

The following non-limiting examples illustrate the invention.

EXAMPLES

The metallocene compound (A) employed in these examples are as follows:

catalyst A: rac-ethylenebis(tetrahydroindenyl)zirconium dimethyl catalyst B: bis(cyclopentadienyl)zirconium dichloride catalyst C: diphenylmethylene(cyclopentadienyl-9-fluorenyl)zirconium dichloride catalyst D: isopropylidene-2-(2-methylindenyl)-2-(3-tert-butylcyclopentadienyl)zirconium dichloride catalyst E: rac-Dimethylsilyl-bis[2-methyl-4-phenylindenyl]-zirconium dichloride Catalyst A is in compliance with the invention, whereas catalysts B to E are comparative.

The 1-decene used for all the experiments was purchased from TCI or Acros at purity of more than 94% and further purified 3 Å molecular sieves and 13× molecular sieves available from Sigma-Aldrich®. The molecular sieves have been dried at 200° C. during at least 16 hours before use.

These solvents or diluents used are usually pre-treated in the same manner as the feed olefins, i.e. they were purified over 3 Å molecular sieves and 13× molecular sieves available from Sigma-Aldrich®. The molecular sieves have been dried at 200° C. during at least 16 hours before use.

GPC on low viscosity (<100 cSt) polyalpha-olefins obtained by metallocene-catalyzed oligometizations (mPAOs) was performed at 35° C. in THF (polystyrene conditions). Molecular weights of high viscosity mPAOs were determined at 135° C. in TCB. Kinematic viscosity was performed at 100° C. according to ASTM D445.

Examples 1-8

The oligomerization reactions were performed in a 20 mL autoclave reactor with a magnetic agitator, a temperature controller and inlets for the feeding of nitrogen, hydrogen.

The catalyst was activated with MAO at an activator/catalyst molar ratio Al/Zr=1000.

The reactor was dried at 130° C. with nitrogen during one hour and then cooled to 110° C. prior to use. Then the reactor was filled under argon or nitrogen, with 20 mL of a solution of 1-decene in cyclohexane, the solution comprising 47.5 wt % of 1-decene relative to the total weight of the solution prior to the introduction of the catalysts components. The reactor is quickly brought up to the desired temperature and when necessary, hydrogen was added at a determined pressure. The metallocene catalyst concentration is of 10-20 μM relative to the oligomerization solution. After 60-90 min, 1 mL of isopropanol were introduced to the reactor to deactivate the catalyst. Residues of monomer were removed by vacuum distillation.

The results are displayed and commented in the following tables.

TABLE 1

| Oligomerization of 1-decene - Influence of the catalyst structure | | | |
|---|---|---|---|
| | Ex 1 | Ex 2 (comp) | Ex 3 (comp) |
| Temperature (° C.) | 80 | 80 | 80 |
| Catalyst | A | B | C |
| Catalyst concentration (μM) | 15 | 15 | 15 |
| Activator | MAO | MAO | MAO |
| Pressure $H_2$ (bar) | 5 | 5 | 5 |
| Time reaction (min) | 75 | 75 | 75 |
| Activity (kg Lube $mmol^{-1}$ Zr $h^{-1}$) | 11.6 | 5.2 | 21.4 |
| Mw (Da) | 3,245 | ND | 27,693 |
| Mw/Mn | 1.6 | ND | 2.3 |
| Calc KV 100 (cSt) | 28 | ND | 612 |

ND = not determined

The molecular weight determined by GPC was converted into a kinematic viscosity at 100° C. using the following empirical relationships: if Mw>2000 Da then Calc KV 100 (cSt)=(0.0239×Mw)−49.581; If 1500<Mw<2000 Da then Calc KV 100 (cSt)=(0.0079×Mw)−5.5342.

From table 1, it can be seen that catalyst B has less activity than catalyst A at the same hydrogen pressure. The molecular weight of the product of Ex. 2 was not determined because of the low activity of Catalyst B. Catalyst C shows high viscosity even in the presence of hydrogen in the oligomerization's reactor. However, the catalyst C does not allow obtaining polyalpha-olefins in the targeted range of kinematic viscosity at 100° C.

Hydrogen is used to regulate the molecular weight which is proportional to the kinematic viscosity. It can be seen from the results (Table 2) that the addition of hydrogen results in an increase of catalyst's activity which is more pronounced for catalyst D than for catalyst A. However, low kinematic viscosity at 100° C. of below 50 cSt, is not reached with catalyst D. The addition of hydrogen in the reactor also results in hydrogenation of 1-decene, thus the use of hydrogen as transfer agent for the metallocene catalyst is to be limited to avoid high levels of hydrogenation of the feedstock.

TABLE 2

| Oligomerization of 1-decene - Influence of hydrogen pressure | | | | | | |
|---|---|---|---|---|---|---|
| | Ex 4 (comp) | Ex 1 | Ex 5 | Ex 6 (comp) | Ex 7 (comp) | Ex 8 (comp) |
| Temperature | 80 | 80 | 80 | 80 | 80 | 80 |
| Catalyst | A | A | A | D | D | D |
| Catalyst concentration (μM) | 15 | 15 | 15 | 15 | 15 | 15 |
| Activator | MAO | MAO | MAO | MAO | MAO | MAO |
| Pressure $H_2$ (bar) | 0 | 5 | 15 | 0 | 5 | 15 |
| Time reaction (min) | 75 | 75 | 75 | 75 | 75 | 75 |
| Activity (kg Lube $mmol^{-1}$ Zr $h^{-1}$) | 11.7 | 11.6 | 18.3 | 10.4 | 16.2 | 27.3 |
| Mw (Da) | 6,294 | 3,245 | 3,414 | 8,056 | 5,065 | 5,683 |
| Mw/Mn | 1.7 | 1.6 | 2 | 2.1 | 2.1 | 2.3 |
| Calc KV 100 (cSt) | 101 | 28 | 32 | 143 | 71 | 86 |

TABLE 2-continued

Oligomerization of 1-decene - Influence of hydrogen pressure

|  | Ex 4 (comp) | Ex 1 | Ex 5 | Ex 6 (comp) | Ex 7 (comp) | Ex 8 (comp) |
|---|---|---|---|---|---|---|
| wt % C10 hydrogenated | ND | ND | 31.5 | ND | ND | 14.0 |

The content of C10 hydrogenated is determined by GC on a HP6890 chromatograph using a HP5 apolar (30 m×250 μm×0.25 μm) capillary column. Samples were solubilised in dichloromethane prior to injection of 1 μL. Column flow: 1.2 mL/min (MS); 1.5 mL/min (FID).

Injector temperature: 280° C.; split flow 50 mL/min. Ramping program: start isotherm at 50° C. then ramping from 50 to 300° C. at 10° C./min. Isotherm at 300° C. for 50 min. Mass detector: 26-800; electronic impact for identification. FID detector: 250° C. for quantification.

Examples 9 and 10

The same procedure than for examples 1 to 8 is used except that 1-decene is added pure (not in solution in cyclohexane).

From table 3 it can be seen that the higher oligomerization temperature results in the formation of lower viscosity mPAOs. However, catalyst E does not allow the obtaining of mPAOs showing low kinematic viscosity at 100° C. (i.e. below 30 cSt) in the same conditions. As both catalysts A and E are racemic bridged metallocene catalysts, these examples further illustrate the differences on the products obtained resulting from the selection of the catalyst.

TABLE 3

Oligomerization of 1-decene - Influence of the temperature

|  | Ex 1 | Ex 9 | Ex 10 (comp) |
|---|---|---|---|
| Temperature (° C.) | 80 | 120 | 120 |
| Catalyst | A | A | E |
| Activator | MAO | MAO | MAO |
| Pressure H$_2$ (bar) | 5 | 5 | 5 |
| Activity (kg Lube mmol$^{-1}$ Zr h$^{-1}$) | 11.6 | ND | ND |
| Mw (Da) | 3,245 | 1,986 | 6,341 |
| Mw/Mn | 1.6 | 2.7 | 3.3 |
| Calc KV 100 (cSt) | 28 | 10.15 | 102 |

From table 3 it can be seen that the higher oligomerization temperature results in the formation of lower viscosity mPAOs. However, catalyst E does not allow the obtaining of mPAOs showing low kinematic viscosity at 100° C. (i.e. below 30 cSt) in the same conditions. As both catalysts A and E are racemic bridged metallocene catalysts, these examples further illustrate the differences on the products obtained resulting from the selection of the catalyst.

Examples 11 to 14

The oligomerization reactions were performed in a 0.95 liter autoclave reactor with an agitator, a temperature controller and inlets for the feeding of nitrogen, hydrogen and 1-decene.

The reactor was dried at 130° C. with nitrogen during one hour and then cooled to 110° C. prior to use. Then the reactor was filled under argon or nitrogen, with 350 mL of 1-decene and the desired volume of hydrogen. Triisobutylaluminum (TiBAl) was also introduced as an impurity scavenger in an amount of 2 mL (10% w/w in n-hexane). The reactor is brought up to the desired temperature and pressure prior to the introduction of the catalysts components. Oligomerization was started upon addition of the metallocene catalyst at a concentration of 20-32 μM relative to the oligomerization solution. After 120 min, 5 mL of isopropanol were introduced to the reactor to deactivate the catalyst. After oligomerization, the crude product was hydrogenated at 50 bar H$_2$ and 100° C. in the presence of 0.5 g Pd/Al$_2$O$_3$ for 4 hours. Residues of monomer were removed by vacuum distillation.

For examples 11 and 12, the activator was MAO used with a molar ratio Al/Zr=1000.

For examples 13 and 14, the activator was DMAB/TiBAl used with a molar ratio B/Zr=1.0 and Al/Zr=200.

The results from table 4 show that the activity of the catalyst can be further enhanced by using an ionic activator instead of an alumoxane. However, in case of using an ionic activator, higher temperature increases the dimer content in a more pronounced way than for an alumoxane activator. Ionic activators are therefore preferably used in association of a temperature of oligomerization below 130° C.

TABLE 4

Oligomerization of 1-decene - Influence of the activator

|  | Ex 11 | Ex 12 | Ex 13 | Ex 14 |
|---|---|---|---|---|
| Temperature (° C.) | 120 | 140 | 120 | 140 |
| Catalyst | A | A | A | A |
| Catalyst concentration (μM) | 26 | 26 | 26 | 26 |
| Activator | MAO | MAO | DMAB/TiBAl | DMAB/TiBAl |
| ratio H$_2$/monomer (ppm)[1] | 410 | 220 | 110 | 320 |
| Activity (kg Lube mmol$^{-1}$ Zr h$^{-1}$) | 14.8 | 11.5 | 17.5 | 18.5 |
| Productivity (kg Lube g$^{-1}$ cat) | 66.8 | 52 | 80.9 | 85.4 |
| Yield %[2] | 90 | 73 | 71 | 74 |
| % C20[3] | 29.0 | 38.7 | 29.0 | 57.2 |
| Mw (Da) | 1,369 | 1,340 | 1,203 | 605 |
| Mw/Mn | 2.3 | 2.0 | 1.3 | 1.6 |
| KV 100 (cSt) | 6.8 | 6.0 | 5.5 | 2.6 |
| KV 40 (cSt) | 33.5 | 27.5 | 24.9 | 8.5 |
| Viscosity index | 168 | 170 | 164 | 140 |

[1]The ratio H$_2$/monomer is calculated in mol %.
[2]Yield determined without hydrogenation after removal of volatiles by distillation at 100° C. and 1 mbar.
[3]Dimer content in the final product determined by gas chromatography.

Example 15

The oligomerization reactions were performed in a 8 liter autoclave reactor with an agitator, a temperature controller and inlets for the feeding of nitrogen, hydrogen and 1-decene. 75 ppm of TiBAl were added as scavenger. The catalyst was activated with DMAB used with a molar ratio B/Zr=1.

The reactor was dried at 130° C. with nitrogen during one hour and then cooled to 110° C. prior to use.

Then the reactor was filled under argon or nitrogen, with 3500 mL of 1-decene. The reactor is brought up to the desired temperature and desired amount of hydrogen was introduced prior to the introduction of the catalysts components. Oligomerization was started upon addition of the metallocene catalyst at a concentration of 17 μM relative to the oligomerization solution. After 120 min, 5 mL of isopropanol were introduced to the reactor to deactivate the catalyst. Hydrogenation reaction was conducted using palladium on alumina under 20 bar of hydrogen at 100° C. during 4 hours. The hydrogenation catalyst was palladium 5% on gamma alumina, purchased from Alfa Aesar.

The C30 fraction has been isolated by distillation using ASTMD2892 under 0.5 mmHg partial pressure as a cut having an atmospheric equivalent boiling temperature range from 350 to 440° C. The resulting C30 fraction contains a mixture comprising 9-methyl-11-octylhenicosane and 11-octyldocosane.

TABLE 5

Results on the oligomers

|  | Ex 13 | Ex 15 |
|---|---|---|
| Temperature (° C.) | 120 | 110 |
| Catalyst | A | A |
| Activator | DMAB/TiBAl | DMAB/TiBAl |
| ratio $H_2$/monomer (ppm)[1] | 110 | 414 |
| wt % conversion[2] | 87 | 92 |
| % C30 in converted material[2] | 26.5 | 23.8 |
| wt % of 11-octyldocosane in the C30 fraction[4] | ND | 9 |
| Unsaturation[3] - mol % trisubstitued olefins in C30 fraction | ND | 21 |
| Unsaturation[3] - mol % vinylidene in C30 fraction | ND | 68 |
| Unsaturation[3] - mol % 1,2-disubstuted olefins fraction | ND | 11 |
| KV 100 (cSt) | 5.5 | 3.5 |
| Viscosity index | 164 | 182 |

ND = not determined
[1]The ratio $H_2$/monomer is calculated in % wt.
[2]wt % conversion and % C30 in converted material was determined using simulated distillation according to ASTM 2887.
[3]Unsaturations were determined by 1H NMR method.
[4]Determined by 1H NMR after C30 fraction isolation using distillation according to ASTM D2892.

The 1H NMR analysis (used to measure 1,2-disubstitutions) was performed under conditions such that the signal intensity in the spectrum is directly proportional to the total number of contributing hydrogen atoms in the sample. Such conditions are well known to the skilled person and include sufficient relaxation time. In practice, the intensity of a signal is obtained from its integral, i.e. the corresponding area. The data were acquired using several tenths or hundreds scans per spectrum, at a temperature of 25° C. The sample was prepared by dissolving 150 to 300 mg of C30 fraction in 2.5 mL of deuterated chloroform, followed by the addition of 2 drops of tetramethylsilane (TMS) as internal standard.

The chemical shifts are referenced to the signal of the internal standard TMS, which is assigned to a value of 0.0 ppm. The olefinic region comprises the signal from the unsaturated part of the C30 fraction and is used to determine the composition of the C30 fraction from the branch methyl resonances.

1H observed signals from the olefinic region are assigned according to the paper by Kim, I I.; Zhou, J-M. and Chung, H. *Journal of polymer science: Part A: Polymer Chemistry* 2000, 38, 1687-1697. The chemical shift assignments are presented in the table below.

The integral values can be normalized according to the proton multiplicity to give the mole-percentage of each olefin class.

| Olefin type | Chemical shift range | Number of protons |
|---|---|---|
| Vinyl (CH=$CH_2$) | 5.7-5.9 | 1 |
| Vinyl (CH=$CH_2$) | 4.8-5.3 | 2 |
| 1,2-disubstituted (CH=CH) | 5.3-5.6 | 2 |
| Trisubstituted (CH=C) | 4.85-5.3 | 1 |
| Vinylidene (all forms, $CH_2$=C) | 4.6-4.85 | 2 |

1,2-disubstituted olefins were used in non hydrogenated C30 samples to determine the amount of 11-octyldocosane in hydrogenated samples as 1,2-disubstituted C30 olefins lead to 11-octyldocosane after hydrogenation.

Surprisingly, the use of the metallocene catalyst according to the invention in presence of hydrogen has an unexpected good selectivity toward C30 oligomers, i.e. a % C30 converted material of more than 20 wt %. This result is coupled to an unexpected content of 11-octyldocosane in the C30 fraction i.e. the content of 11-octyldocosane in the C30 fraction is at least 9 wt % relative to the total weight of the C30 fraction, and an unexpected content of unsaturations.

WO2007/011459 demonstrates the importance of the selection of the catalyst to obtain targeted properties. The examples given are related to oligomerization reaction in the absence of hydrogen. Only comparative examples 1 to 4 of WO2007/011459 are produced in the presence of hydrogen during the oligomerization step. These comparative examples show that the content of 11-octyldocosane in the C30 fraction is below 8 mol % and that the $KV_{100}$ is above 50 cSt. Example 30 to 33 of WO2007/011459 were performed with catalyst rac-dimethysilylbis(tetrahydroindenyl) zirconium dichloride in the absence of hydrogen during the oligomerization step. The absence of hydrogen in Ex 33 allows a higher degree of unsaturation and an higher content of 11-octyldocosane in the C30 fraction than in the comparative examples 1 to 4. Example 30 is performed at 126° C. and shows a content of 8.4 wt % of 11-octyldocosane in the C30 fraction, a KV 100 of 15.86 cSt and a VI of 169. Example 31 is performed at 100° C. and shows a content of 11.3 wt % of 11-octyldocosane in the C30 fraction, a KV 100 of 37.56 cSt and a VI of 183.

Thus, obtaining, according to the invention, a content of at least 9 wt % of 11-octyldocosane in the C30 fraction together with a $KV_{100}$ below 5 cSt and a VI of about 180, in example 15 (performed at 110° C.), was unexpected from previously known chemistry.

The results on unsaturation are also unexpected. In WO2007/011459, examples 33 and 76 are performed in the absence of hydrogen and have a content of 10 to 17 mol % of the unsaturation double bonds to be trisubstitued olefins, compared to 52 mol % of trisubstitued olefins obtained with comparative Example 4 performed in the presence of hydrogen. Surprisingly example 15 of the invention has a content of only 21 mol % of trisubstitued olefins in the PAOs obtained in the presence of hydrogen during the oligomerization step. A similar observation can be made regarding 1,2-disubstituted olefins. Example 15 of the invention has a content of 11 mol % obtained in presence of hydrogen. In WO2007/011459 examples 33 and 76, where no hydrogen was added to the reactor, have a content of 1,2-disubstituted olefins of 11.6 to 19 mol % in contrast to comparative example 4, where oligomerization was performed under a pressure of hydrogen of 200 psi and has a content of 1,2-disubstituted olefins of only 7 mol %.

Regarding now the catalyst productivity, the inventive use allows obtaining more than 80 kg Lube $g^{-1}$ cat (see inventive Examples 13 and 14), whereas the productivity of rac-dimethysilylbis(tetrahydroindenyl)zirconium dichloride together with an ionic activator as described in examples 39 and 40 of WO2007/011459 only reach 18 kg Lube g$^{-1}$ cat.

Thus the use according to the invention offers therefore an improved compromise between the structural properties of the PAOs resulting in an improved viscometrics (i.e. a good compromise between kinematic viscosity and viscosity index), together with an improved catalyst activity.

The invention claimed is:

1. A process comprising:
   homo-oligomerization of olefin monomers by contacting the olefin monomers and a racemic bridged metallocene catalyst comprising a metallocene compound (A) and an activator component (B) at a temperature of 80° C. to 150° C. in the presence of hydrogen; and
   recovering an effluent containing polyalpha-olefins (PAOs), wherein the polyalpha-olefins (PAOs) have a kinematic viscosity of from 2 to 50 cSt, as measured according to ASTM D445 at 100° C. and a molecular weight (Mw) of 30,000 Da or less;
   wherein the metallocene compound (A) is represented by the formula $R(Cp_1)(Cp_2)MX_1X_2$;

wherein R is ethylene (—CH$_2$—CH$_2$—), 1-methyl-ethylene (—CH(CH$_3$)—CH$_2$), n-propylene (—CH$_2$—CH$_2$—CH$_2$—), 2-methylpropylene (—CH$_2$—CH(CH$_3$)—CH$_2$—), 3-methylpropylene (—CH$_2$—CH$_2$—CH(CH$_3$)—), n-butylene (—CH$_2$—CH$_2$—CH$_2$—CH$_2$—), 2-methylbutylene (—CH$_2$—CH(CH$_3$)—CH$_2$—CH$_2$—), 4-methylbutylene (—CH$_2$—CH$_2$—CH$_2$—CH(CH$_3$)—), pentylene and its chain isomers, hexylene and its chain isomers, heptylene and its chain isomers, octylene and its chain isomers, nonylene and its chain isomers, decylene and its chain isomers, undecylene and its chain isomers, dodecylene or its chain isomers;
   wherein Cp$_1$ and Cp$_2$ are the same or different substituted or unsubstituted tetrahydroindenyl rings;
   wherein M is a transition metal selected from the group consisting of titanium, zirconium and hafnium;
   wherein X$_1$ and X$_2$ are independently selected from the group consisting of hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, and substituted germylcarbyl radicals; or wherein both X$_1$ and X$_2$ are joined and bound to the metal atom to form a metallacycle ring containing from 3 to 20 carbon atoms.

2. The process of claim 1, wherein, in the metallocene compound (A), R is ethylene.

3. The process of claim 1, wherein, in the metallocene compound (A), M is zirconium.

4. The process of claim 1, wherein the metallocene compound (A) is racemic ethylene bis(tetrahydroindenyl) zirconium dimethyl.

5. The process of claim 1, wherein the metallocene compound (A) is racemic ethylene bis (tetrahydroindenyl) zirconium dichloride.

6. The process of claim 1, wherein the activator component (B) is an alumoxane selected from the group consisting of methylalumoxane, modified methyl alumoxane, ethylalumoxane, isobutylalumoxane, and combinations thereof.

7. The process of claim 1, wherein the activator component (B) is methylalumoxane (MAO).

8. The process of claim 1, wherein the activator component (B) is an ionic activator selected from the group consisting of dimethylanilinium tetrakis(perfluorophenyl) borate, triphenylcarbonium tetrakis(perfluorophenyl)borate, dimethylanilinium tetrakis(perfluorophenyl)aluminate, and combinations thereof.

9. The process of claim 8, wherein the ionic activator is dimethylanilinium tetrakis(perfluorophenyl)borate.

10. The process of claim 8, wherein the ionic activator is used in combination with a co-activator, and wherein the co-activator is a trialkylaluminium selected from the group consisting of Tri-Ethyl Aluminum (TEAL), Tri-Iso-Butyl Aluminum (TIBAL), Tri-Methyl Aluminum (TMA), and Methyl-Methyl-Ethyl Aluminum (MMEAL).

11. The process of claim 10, wherein the co-activator is Tri-Iso-Butyl Aluminum (TIBAL).

12. The process of claim 1, further comprising, conducting a hydrogenation reaction before recovering the effluent containing polyalpha-olefins (PAOs).

13. The process of claim 12, wherein the hydrogenation reaction is performed with a hydrogenation catalyst selected from the group consisting of nickel supported on kieselguhr, platinum or palladium supported on alumina, and cobalt-molybdenum supported on alumina.

14. The process of claim 13, wherein the hydrogenation catalyst is palladium supported on alumina.

15. The process of claim 1, wherein the contacting of the olefin monomers and the racemic bridged metallocene catalyst at a temperature of 80° C. to 150° C. in the presence of hydrogen is performed in a reactor in a batch mode.

16. The process of claim 1, wherein the olefin monomers comprise 1-decene.

17. A process comprising:
   homo-oligomerization of olefin monomers by contacting the olefin monomers and a racemic bridged metallocene catalyst comprising a metallocene compound (A) and an activator component (B) in the presence of hydrogen; and
   recovering an effluent containing polyalpha-olefins (PAOs), wherein the polyalpha-olefins (PAOs) have a kinematic viscosity of from 2 to 50 cSt, as measured according to ASTM D445 at 100° C. and a molecular weight (Mw) of 30,000 Da or less;
   wherein the metallocene compound (A) is represented by the formula $R(Cp_1)(Cp_2)MX_1X_2$;

wherein R is ethylene (—CH$_2$—CH$_2$—), 1-methyl-ethylene (—CH(CH$_3$)—CH$_2$), n-propylene (—CH$_2$—CH$_2$—CH$_2$—), 2-methylpropylene (—CH$_2$—CH(CH$_3$)—CH$_2$—), 3-methylpropylene (—CH$_2$—CH$_2$—CH(CH$_3$)—), n-butylene (—CH$_2$—CH$_2$—CH$_2$—CH$_2$—), 2-methylbutylene (—CH$_2$—CH(CH$_3$)—CH$_2$—CH$_2$—), 4-methylbutylene (—CH$_2$—CH$_2$—CH$_2$—CH(CH$_3$)—), pentylene and its chain isomers, hexylene and its chain isomers, heptylene and its chain isomers, octylene and its chain isomers, nonylene and its chain isomers, decylene and its chain isomers, undecylene and its chain isomers, dodecylene or its chain isomers;
   wherein Cp$_1$ and Cp$_2$ are the same or different substituted or unsubstituted tetrahydroindenyl rings;
   wherein M is a transition metal selected from the group consisting of titanium, zirconium and hafnium;
   wherein X$_1$ and X$_2$ are independently selected from the group consisting of hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, and substituted germylcarbyl radicals; or wherein both $X_1$ and $X_2$ are joined and bound to the metal atom to form a metallacycle ring containing from 3 to 20 carbon atoms.

18. The process of claim 1, wherein the polyalpha-olefins (PAOs) have a kinematic viscosity of from 3 to 30 cSt, as measured according to ASTM D445 at 100° C.

19. The process of claim 1, wherein the polyalpha-olefins (PAOs) have a kinematic viscosity of from 3 to 10 cSt, as measured according to ASTM D445 at 100° C.

20. The process of claim 1, wherein $Cp_1$ and $Cp_2$ are substituted tetrahydroindenyl rings, wherein the substitutions are independent.

21. The process of claim 1, wherein $Cp_1$ and $Cp_2$ are substituted tetrahydroindenyl rings, wherein the substitutions are linked to form multicyclic structures.

22. A process comprising:
contacting olefin monomers and a racemic bridged metallocene catalyst comprising a metallocene compound (A) and an activator component (B) at a temperature of 80° C. to 150° C. in the presence of hydrogen; and
recovering an effluent containing polyalpha-olefins (PAOs), wherein the polyalpha-olefins (PAOs) have a kinematic viscosity of from 2 to 50 cSt, as measured according to ASTM D445 at 100° C. and a molecular weight (Mw) of 30,000 Da or less;
wherein the metallocene compound (A) is represented by the formula

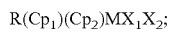

wherein R is ethylene (—CH$_2$—CH$_2$—), 1-methyl-ethylene (—CH(CH$_3$)—CH$_2$), n-propylene (—CH$_2$—CH$_2$—CH$_2$—), 2-methylpropylene (—CH$_2$—CH(CH$_3$)—CH$_2$—), 3-methylpropylene (—CH$_2$—CH$_2$—CH(CH$_3$)—), n-butylene (—CH$_2$—CH$_2$—CH$_2$—CH$_2$—), 2-methylbutylene (—CH$_2$—CH(CH$_3$)—CH$_2$—CH$_2$—), 4-methylbutylene (—CH$_2$—CH$_2$—CH$_2$—CH(CH$_3$)—), pentylene and its chain isomers, hexylene and its chain isomers, heptylene and its chain isomers, octylene and its chain isomers, nonylene and its chain isomers, decylene and its chain isomers, undecylene and its chain isomers, dodecylene or its chain isomers;
wherein $Cp_1$ and $Cp_2$ are the same or different substituted or unsubstituted tetrahydroindenyl rings;
wherein M is a transition metal selected from the group consisting of titanium, zirconium and hafnium;
wherein $X_1$ and $X_2$ are independently selected from the group consisting of hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, and substituted germylcarbyl radicals; or wherein both $X_1$ and $X_2$ are joined and bound to the metal atom to form a metallacycle ring containing from 3 to 20 carbon atoms.

23. The process of claim 22, wherein, in the metallocene compound (A), R is ethylene and M is zirconium.

24. The process of claim 22, wherein the metallocene compound (A) is racemic ethylene bis(tetrahydroindenyl) zirconium dimethyl.

25. The process of claim 1, wherein the polyalpha-olefins (PAOs) comprise a molecular weight distribution (Mw/Mn) of greater than 1 and less than 5.

26. The process of claim 1, wherein the polyalpha-olefins (PAOs) comprise from 2 to 75 mers units.

27. The process of claim 1, wherein the polyalpha-olefins (PAOs) comprise dimers, trimers, and tetramers.

* * * * *